United States Patent
Ishii et al.

(10) Patent No.: US 6,768,023 B2
(45) Date of Patent: Jul. 27, 2004

(54) PROCESS FOR PRODUCING ORGANIC COMPOUNDS USING NITRITES

(75) Inventors: Yasutaka Ishii, Takatsuki (JP); Tatsuya Nakano, Himeji (JP); Takahiro Iwahama, Himeji (JP)

(73) Assignee: Daicel Chemical Industries, Ltd., Osaka (JP)

( * ) Notice: Subject to any disclaimer, the term of this patent is extended or adjusted under 35 U.S.C. 154(b) by 0 days.

(21) Appl. No.: 10/379,600

(22) Filed: Mar. 6, 2003

(65) Prior Publication Data

US 2003/0171618 A1 Sep. 11, 2003

(30) Foreign Application Priority Data

Mar. 7, 2002 (JP) .................................... 2002-062753
Dec. 6, 2002 (JP) .................................... 2002-355420

(51) Int. Cl.$^7$ ............................................. C07C 249/06
(52) U.S. Cl. ..................................... 564/260; 564/261
(58) Field of Search ................................. 564/254, 260, 564/261, 262

(56) References Cited

U.S. PATENT DOCUMENTS 3,544,438 A * 12/1970 de Boer ..................... 204/162
5,719,316 A    2/1998 Ollivier et al.
6,197,999 B1   3/2001 Ollivier et al.

FOREIGN PATENT DOCUMENTS

| JP | 59101456 A | 6/1984 |
| JP | 2-13659 B2 | 4/1990 |
| JP | 2002160910 A | 4/2002 |

OTHER PUBLICATIONS

Database CAPLUS on STN, Acc. No. 2001:663629, JP 2001247486, Sep. 11, 2001, (abstract).*
Database CAPLUS on STN, Acc. No. 1984:570785, JP 59101456, Jun. 12, 1984, (abstract).*
Patent Abstracts XP–002256274 for JP 2002160910, pp. 1–4, (2002).

* cited by examiner

*Primary Examiner*—Brian Davis
(74) *Attorney, Agent, or Firm*—Birch, Stewart, Kolasch & Birch, LLP

(57) ABSTRACT

A process produces an organic compound by allowing (A) a compound capable of generating a free radical to react with (B) at least one of esters and salts of nitrous acid in the presence of a nitrogen-containing cyclic compound constitutively having a skeleton represented by following Formula (i) in its ring:

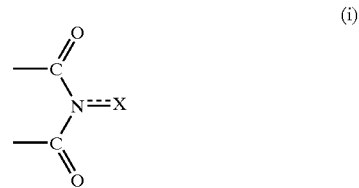

wherein X is an oxygen atom or an —OR group, and wherein R is a hydrogen atom or a hydroxyl-protecting group. Examples of the nitrogen-containing cyclic compound are cyclic imide compounds having a cyclic imide skeleton represented by following Formula (I):

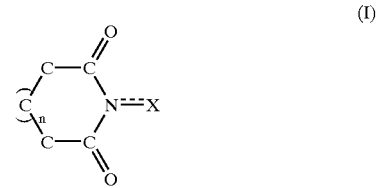

wherein n is 0 or 1; X is an oxygen atom or an —OR group, and wherein R is a hydrogen atom or a hydroxyl-protecting group.

7 Claims, No Drawings

PROCESS FOR PRODUCING ORGANIC COMPOUNDS USING NITRITES

This nonprovisional application claims priority under 35 U.S.C. §119(a) on Patent Application No. 2002-62753 filed in JAPAN on Mar. 7, 2002 and 2002-355420 filed in JAPAN on Dec. 6, 2002, which is herein incorporated by reference.

BACKGROUND OF THE INVENTION

1. Field of the Invention

The present invention relates to a process for producing organic compounds each having, for example, a nitrogen-containing group, an oxygen-containing group, or a carbon-carbon unsaturated bond-containing group using a nitrous ester and/or nitrite.

2. Description of the Related Art

Oximes and other organic compounds each having a nitrogen-containing group are useful as intermediate materials for monomers for the production of polymeric compounds or as intermediates in the synthesis of fine chemicals. For example, cycloalkanone oximes are very important as intermediate materials for polyamides. Such cycloalkanone oximes have been conventionally produced by, for example, a process of subjecting a cycloalkanone and hydroxylamine to dehydration condensation, a process of catalytically hydrogenating a nitrocycloalkenone in the presence of a palladium catalyst, or a process of subjecting a hydroxyaminocycloalkane to air oxidation in the presence of a divalent cobalt. However, these processes require relatively expensive material compounds.

Cyclohexanone oxime is commercially produced by a process in which cyclohexane is irradiated with radiation in the presence of nitrosyl chloride to thereby yield cyclohexanone oxime via nitrosocyclohexane. This process can directly convert cyclohexane into cyclohexanone oxime and can thereby reduce production costs. However, nitrosyl chloride used as a raw material is generally prepared by a reaction between nitrogen monoxide and chlorine, thus invites complicated facilities and decreased operability and imposes heavy loads on the environment.

As a possible solution to these problems, for example, Japanese Examined Patent Application Publication No. 02-13659 discloses a process of allowing a cycloalkane to come in contact with a nitrous ester in a gas phase at a temperature of 150° C. to 400° C. to thereby yield a cycloalkanone oxime. This process, however, requires severe reaction conditions and exhibits a low space-time yield.

SUMMARY OF THE INVENTION

Accordingly, an object of the present invention is to provide a process for easily producing a nitrogen-containing organic compound such as an oxime from low-cost materials under mild conditions.

Another object of the present invention is to provide a process for efficiently producing an organic compound having, for example, a nitrogen-containing group, an oxygen-containing group, or a carbon-carbon unsaturated bond-containing group using an ester or salt of nitrous acid.

Yet another object of the present invention is to provide a process for selectively producing a nitroso compound or a dimer thereof in a high yield.

Still another object of the present invention is to provide a process for selectively and efficiently producing an oxime.

After intensive investigations to achieve the objects, the present inventors have found organic compounds each having, for example, a nitrogen-containing group, an oxygen-containing group, or a carbon-carbon unsaturated bond-containing group can be produced in good yields by allowing a compound capable of generating a free radical to react with at least one of esters and salts of nitrous acid in the presence of a nitrogen-containing cyclic compound having a specific structure. The present invention has been accomplished based on these findings.

Specifically, the present invention provides a process for producing an organic compound, including allowing (A) a compound capable of generating a free radical to react with (B) at least one of esters and salts of nitrous acid in the presence of a nitrogen-containing cyclic compound constitutively having a skeleton represented by following Formula (i) in its ring:

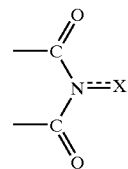

(i)

wherein X is one of an oxygen atom and an —OR group, and wherein R is one of a hydrogen atom and a hydroxyl-protecting group.

By this procedure, oxime compounds and other nitrogen-containing organic compounds having a nitrogen-containing group combined with a radical generating site of the compound (A) capable of generating a free radical; oxygen-containing organic compounds having an oxygen-containing group combined with the radical generating site; and organic compounds having a carbon-carbon unsaturated bond-containing group and other products can be efficiently produced from easily available raw materials by easy and simple procedures under mild conditions.

Examples of the nitrogen-containing cyclic compound include cyclic imide compounds having a cyclic imide skeleton represented by following Formula (I):

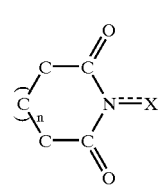

(I)

wherein n is one of 0 and 1; X is one of an oxygen atom and an —OR group, and wherein R is one of a hydrogen atom and a hydroxyl-protecting group.

Examples of the nitrogen-containing cyclic compound also include compounds represented by following Formula (1):

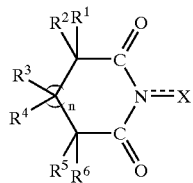

(1)

wherein n is one of 0 and 1;

X is one of an oxygen atom and an —OR group,
wherein R is one of a hydrogen atom and a hydroxyl-protecting group;

$R^1$, $R^2$, $R^3$, $R^4$, $R^5$, and $R^6$ are the same or different and are each one of hydrogen atom, halogen atoms, alkyl groups, aryl groups, cycloalkyl groups, hydroxyl group, alkoxy groups, carboxyl group, substituted oxycarbonyl groups, acyl groups, and acyloxy groups, wherein at least two of $R^1$, $R^2$, $R^3$, $R^4$, $R^5$, and $R^6$ may be combined to form a double bond, an aromatic ring, or a non-aromatic ring with a carbon atom or a carbon-carbon bond constituting the cyclic imide skeleton, and wherein one or more of N-substituted cyclic imide group represented by following Formula (a):

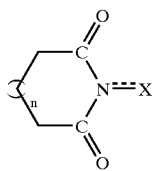

(a)

wherein n and X have the same meanings as defined above, may be further formed on at least one of $R^1$, $R^2$, $R^3$, $R^4$, $R^5$, and $R^6$ or at least one of the double bond, the aromatic ring and the non-aromatic ring formed by at least two of $R^1$, $R^2$, $R^3$, $R^4$, $R^5$, and $R^6$.

Examples of the compound (A) capable of generating a free radical include (A1) aromatic compounds and unsaturated compounds each having a methyl group or methylene group at the adjacent position to an aromatic ring or an unsaturated bond; (A2) non-aromatic cyclic compounds each constitutively having a methylene group in their ring; and (A3) compounds each having a methine carbon atom.

In the process, an oxime compound may be formed as a result of a reaction.

In the process, the nitrous ester or nitrite (B) may be added to reaction system intermittently in plural installments or continuously. By this procedure, a nitroso compound or its dimer, or an oxime compound in a further proceeded reaction can be selectively produced in a high yield. The process may further include allowing the compound (A) capable of generating a free radical to react with the at least one of esters and salts of nitrous acid (B) to thereby yield a nitroso compound or a dimer thereof. The process may also further include the steps of allowing the compound (A) capable of generating a free radical to react with the at least one of esters and salts of nitrous acid (B) to thereby yield a nitroso compound or a dimer thereof; and converting the formed nitroso compound or a dimer thereof into an oxime compound. Thus, an oxime compound can be selectively and efficiently produced.

Further objects, features and advantages of the present invention will become apparent from the following description of the preferred embodiments.

DESCRIPTION OF THE PREFERRED EMBODIMENTS

Nitrogen-Containing Cyclic Compounds

At least one nitrogen-containing cyclic compound constitutively having a skeleton represented by Formula (i) in its ring is used as a catalyst in the present invention.

In Formula (i), the bond between a nitrogen atom and X is a single or double bond. The nitrogen-containing cyclic compound may intramolecularly have a plurality of the skeleton represented by Formula (i). When X is an —OR group and R is a hydroxyl-protecting group, the nitrogen-containing cyclic compound may have a plurality of moieties combined through R, which moieties are derived from the skeleton represented by Formula (i) by removal of R.

Examples of the hydroxyl-protecting group represented by R in Formula (i) are hydroxyl-protecting groups conventionally used in the field of organic synthesis. Such hydroxyl-protecting groups include, but are not limited to, alkyl groups (e.g., methyl, t-butyl, and other $C_1$–$C_4$ alkyl groups), alkenyl groups (e.g., allyl group), cycloalkyl groups (e.g., cyclohexyl group), aryl groups (e.g., 2,4-dinitrophenyl group), aralkyl groups (e.g., benzyl, 2,6-dichlorobenzyl, 3-bromobenzyl, 2-nitrobenzyl, and triphenylmethyl groups); substituted methyl groups (e.g., methoxymethyl, methylthiomethyl, benzyloxymethyl, t-butoxymethyl, 2-methoxyethoxymethyl, 2,2,2-trichloroethoxymethyl, bis(2-chloroethoxy)methyl, and 2-(trimethylsilyl)ethoxymethyl groups), substituted ethyl groups (e.g., 1-ethoxyethyl, 1-methyl-1-methoxyethyl, 1-isopropoxyethyl, 2,2,2-trichloroethyl, and 2-methoxyethyl groups), tetrahydropyranyl group, tetrahydrofuranyl group, 1-hydroxyalkyl groups (e.g., 1-hydroxyethyl, 1-hydroxyhexyl, 1-hydroxydecyl, 1-hydroxyhexadecyl, 1-hydroxy-1-phenylmethyl groups), and other groups capable of forming an acetal or hemiacetal group with a hydroxyl group; acyl groups (e.g., formyl, acetyl, propionyl, butyryl, isobutyryl, valeryl, pivaloyl, hexanoyl, heptanoyl, octanoyl, nonanoyl, decanoyl, lauroyl, myristoyl, palmitoyl, stearoyl, and other aliphatic $C_1$–$C_{20}$ acyl groups, and other aliphatic unsaturated or saturated acyl groups; acetoacetyl group; cyclopentanecarbonyl, cyclohexanecarbonyl, other cycloalkanecarbonyl groups, and other alicyclic acyl groups; benzoyl, naphthoyl, and other aromatic acyl groups), sulfonyl groups (e.g., methanesulfonyl, ethanesulfonyl, trifluoromethanesulfonyl, benzenesulfonyl, p-toluenesulfonyl, and naphthalenesulfonyl groups), alkoxycarbonyl groups (e.g., methoxycarbonyl, ethoxycarbonyl, t-butoxycarbonyl, and other $C_1$–$C_4$ alkoxycarbonyl groups), aralkyloxycarbonyl groups (e.g., benzyloxycarbonyl, and p-methoxybenzyloxycarbonyl groups), substituted or unsubstituted carbamoyl groups (e.g., carbamoyl, methylcarbamoyl, and phenylcarbamoyl groups), groups derived from inorganic acids (e.g., sulfuric acid, nitric acid, phosphoric acid, and boric acid) by removal of OH group, dialkylphosphinothioyl groups (e.g., dimethylphosphinothioyl group), diarylphosphinothioyl groups (e.g., diphenylphosphinothioyl group), and substituted silyl groups (e.g., trimethylsilyl, t-butyldimethylsilyl, tribenzylsilyl, and triphenylsilyl groups).

When X is an —OR group, a plurality of moieties may be combined through R, which moieties are derived from the skeleton of Formula (i) by removal of R. In this case, R includes, for example, oxalyl, malonyl, succinyl, glutaryl, adipoyl, phthaloyl, isophthaloyl, terephthaloyl, and other polycarboxylic acyl groups; carbonyl group; methylene, ethylidene, isopropylidene, cyclopentylidene, cyclohexylidene, benzylidene, and other polyvalent hydrocarbon groups, of which groups capable of forming an acetal bond with two hydroxyl groups are preferred.

Preferred examples of R are hydrogen atom; groups capable of forming an acetal or hemiacetal group (bond) with a hydroxyl group; acyl groups, sulfonyl groups, alkoxycarbonyl groups, carbamoyl groups, and other groups derived from acids (e.g., carboxylic acids, sulfonic acids, carbonic acid, carbamic acid, sulfuric acid, phosphoric acids, and boric acids) by removal of OH group, and other hydrolyzable protecting groups that can be eliminated by hydrolysis.

The nitrogen-containing cyclic compounds include, but are not limited to, cyclic imide compounds each having a N-substituted cyclic imide skeleton represented by Formula (I). These cyclic imide compounds may intramolecularly have a plurality of the N-substituted imide skeleton represented by Formula (I). When X is an —OR group and R is a hydroxyl-protecting group, the cyclic imide compounds may have a plurality of moieties (N-oxy cyclic imide skeletons) combined through R, which moieties are derived from the N-substituted cyclic imide skeleton represented by Formula (I) by removal of R.

In Formula (I), n is 0 or 1. Specifically, Formula (I) represents a five-membered N-substituted cyclic imide skeleton when n is 0 and represents a six-membered N-substituted cyclic imide skeleton when n is 1.

Typical examples of the imide compounds are imide compounds represented by Formula (1). In the substituents $R^1$, $R^2$, $R^3$, $R^4$, $R^5$, and $R^6$ in the imide compounds of Formula (1), the halogen atoms include iodine, bromine, chlorine, and fluorine atoms. The alkyl groups include, for example, methyl, ethyl, propyl, isopropyl, butyl, isobutyl, s-butyl, t-butyl, hexyl, decyl, dodecyl, tetradecyl, hexadecyl, and other straight- or branched-chain alkyl groups each containing from about 1 to about 30 carbon atoms, of which those each containing from about 1 to about 20 carbon atoms are preferred.

The aryl groups include, for example, phenyl, tolyl, xylyl, and naphthyl groups. The cycloalkyl groups include, for example, cyclopentyl and cyclohexyl groups. The alkoxy groups include, for example, methoxy, ethoxy, isopropoxy, butoxy, t-butoxy, hexyloxy, octyloxy, decyloxy, dodecyloxy, tetradecyloxy, octadecyloxy, and other alkoxy groups each containing from about 1 to about 30 carbon atoms, of which alkoxy groups each containing from about 1 to about 20 carbon atoms are preferred.

The substituted oxycarbonyl groups include, but are not limited to, methoxycarbonyl, ethoxycarbonyl, isopropoxycarbonyl, butoxycarbonyl, t-butoxycarbonyl, hexyloxycarbonyl, decyloxycarbonyl, hexadecyloxycarbonyl, and other $C_1$–$C_{30}$ alkoxy-carbonyl groups, of which $C_1$–$C_{20}$ alkoxy-carbonyl groups are preferred; cyclopentyloxycarbonyl, cyclohexyloxycarbonyl, and other cycloalkyloxycarbonyl groups, of which cycloalkyloxycarbonyl groups each having 3 to 20 members are preferred; phenyloxycarbonyl, naphthyloxycarbonyl, and other aryloxycarbonyl groups, of which $C_6$–$C_{20}$ aryloxy-carbonyl groups are preferred; benzyloxycarbonyl, and other aralkyloxycarbonyl groups, of which $C_7$–$C_{21}$ aralkyloxy-carbonyl groups are preferred.

The acyl groups include, but are not limited to, formyl, acetyl, propionyl, butyryl, isobutyryl, valeryl, pivaloyl, hexanoyl, octanoyl, decanoyl, lauroyl, myristoyl, palmitoyl, stearoyl, other aliphatic $C_1$–$C_{30}$ acyl groups, and other unsaturated or saturated aliphatic acyl groups, of which aliphatic $C_1$–$C_{20}$ acyl groups are preferred; acetoacetyl group; cyclopentanecarbonyl, cyclohexanecarbonyl, other cycloalkanecarbonyl, and other alicyclic acyl groups; benzoyl, naphthoyl, and other aromatic acyl groups.

The acyloxy groups include, but are not limited to, formyloxy, acetyloxy, propionyloxy, butyryloxy, isobutyryloxy, valeryloxy, pivaloyloxy, hexanoyloxy, octanoyloxy, decanoyloxy, lauroyloxy, myristoyloxy, palmitoyloxy, stearoyloxy, other aliphatic $C_1$–$C_{30}$ acyloxy groups, and other unsaturated or saturated aliphatic acyloxy groups, of which $C_1$–$C_{20}$ acyloxy groups are preferred; acetoacetyloxy group; cyclopentanecarbonyloxy, cyclohexanecarbonyloxy, other cycloalkanecarbonyloxy, and other alicyclic acyloxy groups; benzoyloxy, naphthoyloxy, and other aromatic acyloxy groups.

The substituents $R^1$, $R^2$, $R^3$, $R^4$, $R^5$, and $R^6$ may be the same with or different from one another. At least two of $R^1$, $R^2$, $R^3$, $R^4$, $R^5$, and $R^6$ in Formula (1) may be combined to form a double bond, an aromatic ring, or a non-aromatic ring with a carbon atom or carbon-carbon bond constituting the cyclic imide skeleton. The aromatic or non-aromatic ring contains preferably from about 5 to about 12 members and more preferably from about 6 to about 10 members. The ring may be a heterocyclic ring or condensed heterocyclic ring, but it is often a hydrocarbon ring. Such rings include, for example, non-aromatic alicyclic rings (e.g., cyclohexane ring and other cycloalkane rings which may have at least one substituent, cyclohexene ring and other cycloalkene rings which may have at least one substituent), non-aromatic bridged rings (e.g., 5-norbornene ring and other bridged hydrocarbon rings which may have at least one substituent), benzene ring, naphthalene ring, and other aromatic rings (including condensed rings) which may have at least one substituent. The ring often comprises an aromatic ring. The ring may have at least one substituent. Such substituents include, but are not limited to, alkyl groups, haloalkyl groups, hydroxyl group, alkoxy groups, carboxyl group, substituted oxycarbonyl groups, acyl groups, acyloxy groups, nitro group, cyano group, amino group, and halogen atoms.

One or more of the N-substituted cyclic imide group represented by Formula (a) may be further formed on at least one of $R^1$, $R^2$, $R^3$, $R^4$, $R^5$, and $R^6$ and/or on the double bond, aromatic ring, or non-aromatic ring formed by the at least two of $R^1$, $R^2$, $R^3$, $R^4$, $R^5$, and $R^6$. For example, when at least one of $R^1$, $R^2$, $R^3$, $R^4$, $R^5$, and $R^6$ is an alkyl group containing two or more carbon atoms, the N-substituted cyclic imide group maybe formed with adjacent two carbon atoms constituting the alkyl group. Likewise, when at least two of $R^1$, $R^2$, $R^3$, $R^4$, $R^5$, and $R^6$ are combined to form a double bond with a carbon-carbon bond constituting the cyclic imide skeleton, the N-substituted cyclic imide group may be formed with the double bond. When at least two of $R^1$, $R^2$, $R^3$, $R^4$, $R^5$, and $R^6$ are combined to form an aromatic or non-aromatic ring with a carbon atom or carbon-carbon bond constituting the cyclic imide skeleton, the N-substituted cyclic imide group may be formed with adjacent two carbon atoms constituting the ring.

Preferred imide compounds include compounds represented by following formulae:

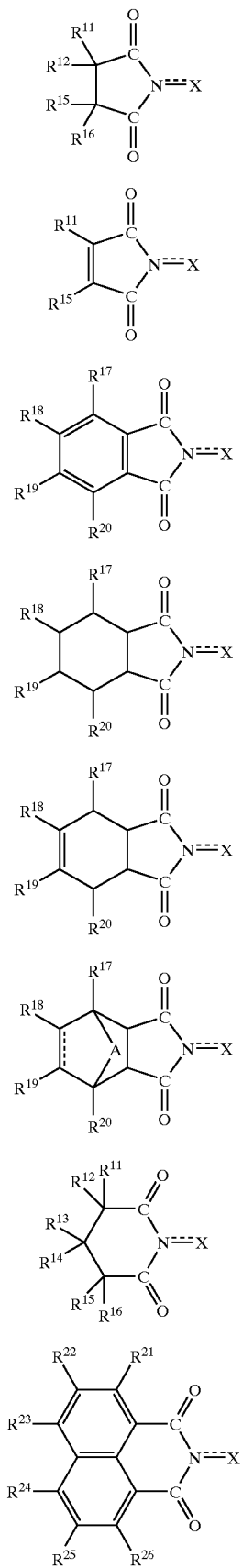

wherein $R^{11}$, $R^{12}$, $R^{13}$, $R^{14}$, $R^{15}$, and $R^{16}$ are the same or different and are each one of hydrogen atom, halogen atoms, alkyl groups, aryl groups, cycloalkyl groups, hydroxyl group, alkoxy groups, carboxyl group, substituted oxycarbonyl groups, acyl groups, and acyloxy groups;

$R^{17}$, $R^{18}$, $R^{19}$, $R^{20}$, $R^{21}$, $R^{22}$, $R^{23}$, $R^{24}$, $R^{25}$, and $R^{26}$ are the same or different and are each one of hydrogen atom, alkyl groups, haloalkyl groups, hydroxyl group, alkoxy groups, carboxyl group, substituted oxycarbonyl groups, acyl groups, acyloxy groups, nitro group, cyano group, amino group, and halogen atoms, wherein adjacent two of $R^{17}$ to $R^{26}$ may be combined to form a five- or six-membered N-substituted cyclic imide skeleton indicated in one of Formulae (1c), (1d), (1e), (1f), (1h), and (1i);

A in Formula (1f) is a methylene group or an oxygen atom; and

X has the same meaning as defined above.

The halogen atoms, alkyl groups, aryl groups, cycloalkyl groups, hydroxyl group, alkoxy groups, carboxyl group, substituted oxycarbonyl groups, acyl groups, and acyloxy groups in the substituents $R^{11}$ to $R^{16}$ include the same groups as in the corresponding groups in the substituents $R^{1}$ to $R^{6}$.

In the substituents $R^{17}$ to $R^{26}$, the alkyl groups include the same alkyl groups as those exemplified above, of which alkyl groups each containing from about 1 to about 6 carbon atoms are preferred. The haloalkyl groups include, for example, trifluoromethyl group, and other haloalkyl groups each containing from about 1 to about 4 carbon atoms. The alkoxy groups include the same alkoxy groups as those exemplified above, of which lower alkoxy groups each containing from about 1 to about 4 carbon atoms are preferred. The substituted oxycarbonyl groups include the same substituted oxycarbonyl groups as those exemplified above, such as alkoxycarbonyl groups, cycloalkyloxycarbonyl groups, aryloxycarbonyl groups, and aralkyloxycarbonyl groups. The acyl groups include aliphatic unsaturated or saturated acyl groups, acetoacetyl group, alicyclic acyl groups, aromatic acyl groups, and other acyl groups as exemplified above. The acyloxy groups include aliphatic unsaturated or saturated acyloxy groups, acetoacetyloxy group, alicyclic acyloxy groups, aromatic acyloxy groups, and other acyloxy groups as exemplified above. The halogen atoms include, for example, fluorine, chlorine, and bromine atoms. Each of the substituents $R^{17}$ to $R^{26}$ is often one of hydrogen atom, lower alkyl groups each containing from about 1 to about 4 carbon atoms, carboxyl group, substituted oxycarbonyl groups, nitro group, and halogen atoms.

Examples of preferred imide compounds having a five-membered N-substituted cyclic imide skeleton are N-hydroxysuccinimide, N-hydroxy-α-methylsuccinimide, N-hydroxy-α,α-dimethylsuccinimide, N-hydroxy-α,β-dimethylsuccinimide, N-hydroxy-α,α,β,β- tetramethylsuccinimide, N-hydroxymaleimide, N-hydroxyhexahydrophthalimide, N,N'-dihydroxycyclohexanetetracarboxylic diimide, N-hydroxyphthalimide, N-hydroxytetrabromophthalimide, N-hydroxytetrachlorophthalimide, N-hydroxychlorendimide, N-hydroxyhimimide, N-hydroxytrimellitimide, N,N'-dihydroxypyromellitic diimide, N,N'-dihydroxynaphthalenetetracarboxylic diimide, α,β-diacetoxy-N-hydroxysuccinimide, N-hydroxy-α,β-bis(propionyloxy)succinimide, N-hydroxy-α,β-bis(valeryloxy)succinimide, N-hydroxy-α,β-bis(lauroyloxy)succinimide, α,β-bis(benzoyloxy)-N-hydroxysuccinimide, N-hydroxy-4-methoxycarbonylphthalimide, 4-chloro-N-hydroxyphthalimide, 4-ethoxycarbonyl-N-hydroxyphthalimide, N-hydroxy-4-pentyloxycarbonylphthalimide, 4-dodecyloxy-N-hydroxycarbonylphthalimide, N-hydroxy-4-phenoxycarbonylphthalimide, N-hydroxy-4,5-bis(methoxycarbonyl)phthalimide, 4,5-bis(ethoxycarbonyl)-N-hydroxyphthalimide, N-hydroxy-4,5-bis(pentyloxycarbonyl)phthalimide, 4,5-bis(dodecyloxycarbonyl)-N-hydroxyphthalimide, N-hydroxy-4,5-bis(phenoxycarbonyl)phthalimide, and other compounds of Formula (1) wherein X is an —OR group and R is a hydrogen atom; compounds corresponding to these compounds, except with R of an acyl group such as acetyl group, propionyl group, and benzoyl group; N-methoxymethyloxyphthalimide, N-(2-methoxyethoxymethyloxy)phthalimide, N-tetrahydropyranyloxyphthalimide, and other compounds of Formula (1) wherein X is an —OR group and R is a group capable of forming an acetal or hemiacetal bond with a hydroxyl group; N-methanesulfonyloxyphthalimide, N-(p-toluenesulfonyloxy)phthalimide, and other compounds of Formula (1) wherein X is an —OR group and R is a sulfonyl group; sulfuric esters, nitric esters, phosphoric esters, and boric esters of N-hydroxyphthalimide, and other compounds of Formula (1) wherein X is an —OR group and R is a group derived from an inorganic acid by removal of OH group.

Examples of preferred imide compounds each having a six-membered N-substituted cyclic imide skeleton are N-hydroxyglutarimide, N-hydroxy-α,α-dimethylglutarimide, N-hydroxy-β,β-dimethylglutarimide, N-hydroxy-1,8-decalindicarboximide, N,N'-dihydroxy-1,8;4,5-decalintetracarboxylic diimide, N-hydroxy-1,8-naphthalenedicarboximide (N-hyrdoxynaphthalimide), N,N'-dihydroxy-1,8;4,5-naphthalenetetracarboxylic diimide, and other compounds of Formula (1) wherein X is an —OR group and R is a hydrogen atom; compounds corresponding to these compounds except with R of an acyl group such as acetyl group, propionyl group, and benzoyl group; N-methoxymethyloxy-1,8-naphthalenedicarboximide, N,N'-bis(methoxymethyloxy)-1,8;4,5-naphthalenetetracarboxylic diimide, and other compounds of Formula (1) wherein X is an —OR group and R is a group capable of forming an acetal or hemiacetal bond with a hydroxyl group; N-methanesulfonyloxy-1,8-naphthalenedicarboximide, N,N'-bis(methanesulfonyloxy)-1,8;4,5-naphthalenetetracarboxylic diimide, and other compounds of Formula (1) wherein X is an —OR group and R is a sulfonyl group; sulfuric esters, nitric esters, phosphoric esters, and boric esters of N-hydroxy-1,8-naphthalenedicarboximide and N,N'-dihydroxy-1,8;4,5-naphthalenetetracarboxylic diimide, and other compounds of Formula (1) wherein X is an —OR group and R is a group derived from an inorganic acid by removal of OH group.

In addition to the cyclic imide compounds, the nitrogen-containing cyclic compounds include, for example, cyclic acylurea compounds each having a cyclic acylurea skeleton [—C(=O)—N—C(=O)—N—] represented by following Formula (II):

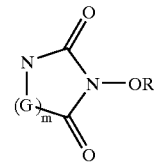

(II)

wherein G is one of a carbon atom and a nitrogen atom; m is one of 1 and 2, and, when m is 2, two Gs may be the same or different; and R has the same meaning as defined above. These cyclic acylurea compounds may each intramolecularly have a plurality of the cyclic acylurea skeleton represented by Formula (II). They also may have a plurality of moieties (N-oxy cyclic acylurea skeletons) combined through R, which moieties are derived from the cyclic acylurea skeleton of Formula (II) by removal of R. The atom G and the nitrogen atom combined with G constituting the cyclic acylurea skeleton may have at least one substituent. The cyclic acylurea skeleton may further have a non-aromatic or aromatic ring condensed therewith and/or may have a double bond in its ring.

The cyclic acylurea skeletons represented by Formula (II) include a 3-hydroxy (or 3-substituted oxy) hydantoin skeleton represented by following Formula (IIa); a 4-hydroxy (or 4-substituted oxy)-1,2,4-triazolidine-3,5-dione skeleton [inclusive of a 4-hydroxy (or 4-substituted oxy)-1,2,4-triazoline-3,5-dione skeleton]] represented by following Formula (IIb); a hydro-3-hydroxy (or 3-substituted oxy)-1,3-diazine-2,4-dione skeleton [inclusive of a hexahydro-1-hydroxy (or 1-substituted oxy)-1,3-diazine-2,4,6-trione skeleton, a hexahydro-1,3-dihydroxy (or 1,3-bis-substituted oxy)-1,3-diazine-2,4,6-trione skeleton, and a 3-hydroxy (or 3-substituted oxy) uracil skeleton] represented by following Formula (IIc); a hydro-4-hydroxy (or 4-substituted oxy)-1,2,4-triazine-3,5-dione skeleton represented by following Formula (IId); a hydro-1-hydroxy (or 1-substituted oxy)-1,3,5-triazine-2,6-dione skeleton represented by following Formula (IIe); and a hydro-5-hydroxy (or 5-substituted oxy)-1,2,3,5-tetrazine-4,6-dione skeleton represented by following Formula (IIf):

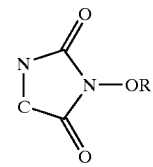

(IIa)

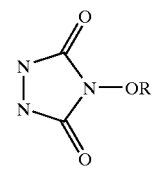

(IIb)

-continued

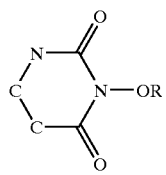
(IIc)

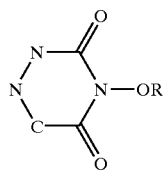
(IId)

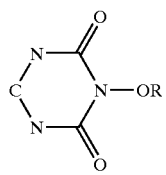
(IIe)

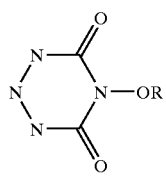
(IIf)

wherein R has the same meaning as defined above.

Typical examples of the cyclic acylurea compounds are hydro-1-hydroxy (or 1-substituted oxy)-1,3,5-triazine-2,6-dione compounds represented by following Formula (2):

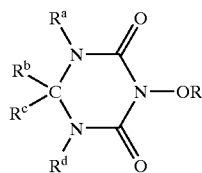
(2)

wherein $R^a$ and $R^d$ are the same or different and are each one of hydrogen atom, alkyl groups, aryl groups, cycloalkyl groups, hydroxyl groups which may be protected by a protecting group, carboxyl groups which may be protected by a protecting group, and acyl groups;

$R^b$ and $R^c$ are the same or different and are each one of hydrogen atom, halogen atoms, alkyl groups, aryl groups, cycloalkyl groups, hydroxyl group, alkoxy groups, carboxyl group, substituted oxycarbonyl groups, acyl groups, and acyloxy groups, wherein at least two of $R^a$, $R^b$, $R^c$, and $R^d$ may be combined to form one of a double bond, an aromatic ring, or a non-aromatic ring with an atom constituting the ring in the formula, wherein $R^b$ and $R^c$ may together form an oxo group; and R has the same meaning as defined above.

In Formula (2), the alkyl groups, aryl groups, cycloalkyl groups, and acyl groups in $R^a$ and $R^b$ are similar to those exemplified in the substituents $R^1$ to $R^6$. The hydroxyl-protecting group herein includes similar hydroxyl-protecting groups as exemplified above.

Examples of the carboxyl-protecting group include protecting groups conventionally used in the field of organic synthesis. Such carboxyl-protecting groups include, but are not limited to, methoxy, ethoxy, butoxy, and other $C_1$–$C_6$ alkoxy groups, and other alkoxy groups; cycloalkyloxy groups; phenoxy group, and other aryloxy groups; benzyloxy, and other aralkyloxy groups; trimethylsilyloxy group, and other trialkylsilyloxy groups; amino group, methylamino group, dimethylamino group, and other mono- or di-$C_1$–$C_6$ alkyl-amino groups, and other amino groups which may have at least one substituent.

Examples of the halogen atoms, alkyl groups, aryl groups, cycloalkyl groups, hydroxyl group, alkoxy groups, carboxy group, substituted oxycarbonyl groups, acyl groups, and acyloxy groups in $R^b$ and $R^c$ are similar to those exemplified in the substituents $R^1$ to $R^6$.

At least two of $R^a$, $R^b$, $R^c$, and $R^d$ may be combined to form one of a double bond, an aromatic ring, and a non-aromatic ring with at least one atom (a carbon atom and/or a nitrogen atom) constituting the ring in Formula (2), and $R^b$ and $R^c$ may together form an oxo group. Preferred examples of the aromatic ring and the non-aromatic ring are similar to those exemplified above.

Preferred examples of the cyclic acylurea compounds are 3-hydroxyhydantoin, 1,3-dihydroxyhydantoin, 3-hydroxy-1-methylhydantoin, 3-acetoxyhydantoin, 1,3-diacetoxyhydantoin, 3-acetoxy-1-methylhydantoin, 3-benzoyloxyhydantoin, 1,3-bis(benzoyloxy)hydantoin, 3-benzoyloxy-1-methylhydantoin, and other compounds each having the skeleton represented by Formula (IIa); 4-hydroxy-1,2,4-triazolidine-3,5-dione, 4-hydroxy-1,2-dimethyl-1,2,4-triazolidine-3,5-dione, 4-acetoxy-1,2,4-triazolidine-3,5-dione, 4-acetoxy-1,2-dimethyl-1,2,4-triazolidine-3,5-dione, 4-benzoyloxy-1,2,4-triazolidine-3,5-dione, 4-benzoyloxy-1,2-dimethyl-1,2,4-triazolidine-3,5-dione, 4-hydroxy-1,2,4-triazoline-3,5-dione, 4-acetoxy-1,2,4-triazoline-3,5-dione, 4-benzoyloxy-1,2,4-triazoline-3,5-dione, and other compounds having the skeleton represented by Formula (IIb); hexahydro-3-hydroxy-1,3-diazine-2,4-dione, hexahydro-1,3-dihydroxy-1,3-diazine-2,4-dione, hexahydro-3-hydroxy-1-methyl-1,3-diazine-2,4-dione, 3-acetoxy-hexahydro-1,3-diazine-2,4-dione, 1,3-diacetoxy-hexahydro-1,3-diazine-2,4-dione, 3-acetoxy-hexahydro-1-methyl-1,3-diazine-2,4-dione, 3-benzoyloxy-hexahydro-1,3-diazine-2,4-dione, 1,3-bis(benzoyloxy)-hexahydro-1,3-diazine-2,4-dione, 3-benzoyloxy-hexahydro-1-methyl-1,3-diazine-2,4-dione, hexahydro-1-hydroxy-1,3-diazine-2,4,6-trione, 1-acetoxy-hexahydro-1,3-diazine-2,4,6-trione, 1-benzoyloxy-hexahydro-1,3-diazine-2,4,6-trione, hexahydro-1,3-dihydroxy-1,3-diazine-2,4,6-trione, 1,3-diacetoxy-hexahydro-1,3-diazine-2,4,6-trione, 1,3-bis(benzoyloxy)-hexahydro-1,3-diazine-2,4,6-trione, 3-hydroxyuracil, 3-acetoxyuracil, 3-benzoyluracil, and other compounds having the skeleton represented by Formula (IIc); hexahydro-4-hydroxy-1,2,4-triazine-3,5-dione, hexahydro-4-hydroxy-1,2-dimethyl-1,2,4-triazine-3,5-dione, 4-acetoxy-hexahydro-1,2,4-triazine-3,5-dione, 4-acetoxy-hexahydro-1,2-dimethyl-1,2,4-triazine-3,5-dione, 4-benzoyloxy-hexahydro-1,2,4-triazine-3,5-dione, 4-benzoyloxy-hexahydro-1,2-dimethyl-1,2,4-triazine-3,5-dione, and other compounds having the skeleton represented by Formula (IId); hexahydro-1,3,5-trihydroxy-1,3,5-triazine-2,4,6-trione, 1,3,5-triacetoxy-hexahydro-1,3,5-triazine-2,4,6-trione, 1,3,5-tris(benzoyloxy)-hexahydro-1,3,5-triazine-2,4,6-trione, hexahydro-1,3,5-tris(methoxymethyloxy)-1,3,5-triazine-2,4,6-trione, hexahydro-1-hydroxy-1,3,5-triazine-2,6-dione, hexahydro-1-hydroxy-3,5-dimethyl-1,3,5-triazine-2,6-dione, 1-acetoxy-hexahydro-1,3,5-triazine-2,6-dione, 1-acetoxyhexahydro-3,5-dimethyl-1,3,5-triazine-2,6-dione, 1-benzoyloxy-hexahydro-1,3,5-triazine-2,6-dione, 1-benzoyloxy-hexahydro-3,5-dimethyl-1,3,5-triazine-2,6-dione, and other compounds having the skeleton represented by Formula (IIe) such as compounds represented by Formula (2); hexahydro-5-hydroxy-1,2,3,5-tetrazine-4,6-dione, hexahydro-5-hydroxy-1,2,3-trimethyl-1,2,3,5-tetrazine-4,6-dione, 5-acetoxy-hexahydro-1,2,3,5-tetrazine-4,6-dione, 5-acetoxy-hexahydro-1,2,3-trimethyl-1,2,3,5-tetrazine-4,6-dione, 5-benzoyloxy-hexahydro-1,2,3,5-tetrazine-4,6-dione, 5-benzoyloxy-hexahydro-1,2,3-trimethyl-1,2,3,5-tetrazine-4,6-dione, and other compounds having the skeleton represented by Formula (IIf).

Among the nitrogen-containing cyclic compounds, compounds wherein X is an —OR group and R is a hydrogen atom (N-hydroxy cyclic compounds) can be prepared according to a known procedure or a combination of such procedures. Compounds wherein X is an —OR group and R is a hydroxyl-protecting group can be prepared by introducing a desired protecting group into a corresponding compound wherein R is a hydrogen atom (N-hydroxy cyclic compounds) according to a conventional reaction procedure for the introduction of protecting groups.

More specifically, among the cyclic imide compounds, compounds wherein X is an —OR group and R is a hydrogen atom (N-hydroxy cyclic imide compounds) can be prepared by a conventional imidization process such as a process that comprises the steps of allowing a corresponding acid anhydride to react with hydroxylamine for ring-opening of an acid anhydride group, and closing the ring to form an imide. For example, N-acetoxyphthalimide can be prepared by allowing N-hydroxyphthalimide to react with acetic anhydride or to react with an acetyl halide in the presence of a base. These compounds can also be prepared by other processes.

Typically preferred imide compounds are N-hydroxysuccinimide, N-hydroxyphthalimide, N,N'-dihydroxypyromellitic diimide, N-hydroxyglutarimide, N-hydroxy-1,8-naphthalenedicarboximide, N,N'-dihydroxy-1,8;4,5-naphthalenetetracarboxylic diimide, and other N-hydroxyimide compounds derived from aliphatic polycarboxylic anhydrides (cyclic anhydrides) or aromatic polycarboxylic anhydrides (cyclic anhydrides); and compounds derived from the N-hydroxyimide compounds by introduction of a protecting group into a hydroxyl group thereof.

Among the cyclic acylurea compounds, for example, 1,3,5-triacetoxy-hexahydro-1,3,5-triazine-2,4,6-trione (i.e., 1,3,5-triacetoxyisocyanuric acid) can be prepared by allowing hexahydro-1,3,5-trihydroxy-1,3,5-triazine-2,4,6-trione (i.e., 1,3,5-trihydroxyisocyanuric acid) to react with acetic anhydride or to react with an acetyl halide in the presence of a base.

Among the nitrogen-containing cyclic compounds, fat-soluble compounds are preferably used as a catalyst in the process of the present invention. In this case, the catalyst can effectively act due to its high solubility even when the reaction is performed in the absence of a solvent or in a low-polarity solvent. The reaction thereby rapidly proceeds to increase productivity and to make separation and purification procedures of target products easier.

Such fat-soluble nitrogen-containing cyclic compounds include, but are not limited to, compounds represented by Formula (1) wherein X is an —OR group and R is a hydrogen atom; at least one of the substituents $R^1$ to $R^6$ and of substituents of the double bond, aromatic ring or non-aromatic ring formed by at least two of $R^1$ to $R^6$ with a carbon atom or carbon-carbon bond constituting the cyclic imide skeleton is a $C_5$–$C_{30}$ acyloxy group or a $C_5$–$C_{30}$ substituted oxycarbonyl group. Typical examples of these compounds are compounds represented by Formula (1a), wherein $R^{11}$ and $R^{16}$ are each an acyloxy group, preferably a $C_5$–$C_{30}$ aliphatic acyloxy group, alicyclic acyloxy group or aromatic acyloxy group, and more preferably a $C_6$–$C_{20}$ aliphatic acyloxy group, a cyclohexylcarbonyl group, or a benzoyloxy group, and $R^{12}$ and $R^{15}$ are hydrogen atoms; compounds represented by Formula (1c), wherein $R^{18}$ is a substituted oxycarbonyl group, preferably a $C_5$–$C_{30}$ alkoxycarbonyl group, a cycloalkyloxycarbonyl group, or an aryloxycarbonyl group, and more preferably a $C_6$–$C_{20}$ alkoxycarbonyl group, a cyclohexyloxycarbonyl group, or a phenoxycarbonyl group, and $R^{17}$, $R^{19}$, and $R^{20}$ are hydrogen atoms; compounds represented by Formula (1c), wherein $R^{18}$ and $R^{19}$ are each a substituted oxycarbonyl group, preferably a $C_5$–$C_{30}$ alkoxy-carbonyl group, a cycloalkyloxycarbonyl group, or an aryloxycarbonyl group, and more preferably a $C_6$–$C_{20}$ alkoxy-carbonyl group, a cyclohexyloxycarbonyl group, or a phenoxycarbonyl group, and $R^{17}$ and $R^{20}$ are hydrogen atoms. Examples of such fat-soluble imide compounds are compounds described as cyclic imide compounds each having a solubility parameter of less than or equal to 26 $[(MPa)^{1/2}]$ as determined by the Fedors' method in European Patent Application Publication No. EP 1238704 A2. The fat-soluble nitrogen-containing cyclic compounds also include cyclic acylurea compounds represented by Formula (II) wherein R is a hydrogen atom; and at least one of $R^b$, $R^c$, and the double bond, aromatic ring, and non-aromatic ring formed by at least two of $R^a$, $R^b$, $R^c$, and $R^d$ with the carbon atom, nitrogen atom, or carbon-carbon (nitrogen) bond constituting the cyclic acylurea skeleton is a $C_5$–$C_{30}$ acyloxy group or a $C_5$–$C_{30}$ substituted oxycarbonyl group.

Each of the nitrogen-containing cyclic compounds having the skeleton represented by Formula (i) as a constituent of their ring can be used alone or in combination in the reaction. For example, a cyclic imide compound having the cyclic imide skeleton of Formula (I) can be used in combination with a cyclic acylurea compound having the cyclic acylurea skeleton of Formula (II). The nitrogen-containing cyclic compound(s) can be formed in the reaction system.

The amount of the nitrogen-containing cyclic compound (s) can be selected within a broad range and is, for example, from about 0.0000001 to about 1 mole, preferably from about 0.000001 to about 0.5 mole, more preferably from about 0.00001 to about 0.4 mole, and often from about 0.0001 to about 0.35 mole per mole of the substrate [the compound (A) capable of generating a free radical (hereinafter briefly referred to as "radical-formable compound (A)")]

Promoters (Co-catalysts)

Where necessary, a promoter (co-catalyst) can be used in combination with the nitrogen-containing cyclic compound catalyst. Such promoters include, but are not limited to, vanadium compounds, manganese compounds, cobalt compounds, compounds of Group 1 and Group 2 metal elements of the Periodic Table of Elements; and organic onium salts. In addition, promoters for imide compound catalysts described in, for example, Japanese Unexamined Patent Application Publication No. 09-327626 can also be used. Each of these promoters can be used alone or in combination. The reaction system may further comprise an initial activator such as a radical initiator, a radical reaction accelerator, and an oxidizing agent.

Radical-formable Compounds (A)

Radical-formable compounds (A) for use in the present invention are not specifically limited as long as they are compounds capable of generating a stable free radical. Typical examples thereof are (A1) aromatic compounds and unsaturated compounds each having a methyl group or methylene group at the adjacent position to an aromatic ring or an unsaturated bond; (A2) non-aromatic cyclic compounds constitutively having a methylene group in their ring; (A3) compounds each having a methine carbon atom; and other compounds having a hydrocarbon moiety capable of generating a free radical.

These compounds may each have at least one substituent within ranges not adversely affecting the reaction. Such substituents include, but are not limited to, alkyl groups(e.g., methyl, ethyl, isopropyl, t-butyl, and other $C_1$–$C_4$ alkyl groups), alkenyl groups (e.g., vinyl, allyl, and other $C_1$–$C_4$ alkenyl groups), alkynyl groups, alicyclic hydrocarbon groups, aromatic hydrocarbon groups (e.g., phenyl, and naphthyl groups), acyl groups, heterocyclic groups, halogen atoms, hydroxyl group, mercapto group, substituted oxy groups (e.g., methoxy, other $C_1$–$C_4$ alkoxy groups, and other alkoxy groups; phenoxy, and other aryloxy groups; and acetyloxy, and other acyloxy groups), substituted thio groups, carboxyl group, substituted oxycarbonyl groups (e.g., methoxycarbonyl, ethoxycarbonyl, other $C_1$–$C_4$ alkoxy-carbonyl, and other alkoxycarbonyl groups), substituted or unsubstituted carbamoyl groups, cyano group, nitro group, substituted or unsubstituted amino groups (e.g., amino group, N,N-dimethylamino, and other N,N-di-$C_1$–$C_4$ alkylamino groups), sulfo group, and groups each comprising a plurality of these groups combined with each other.

The aromatic compounds and unsaturated compounds (A1) each having a methyl group or methylene group at the adjacent position to an aromatic ring or an unsaturated bond include (A1-1) aromatic compounds each having a methyl group or methylene group at the adjacent position (a "benzyl position") to an aromatic ring; and (A1–2) non-aromatic compounds each having a methyl group or methylene group at the adjacent position to an unsaturated bond such as a carbon-carbon unsaturated bond, and a carbon-oxygen double bond).

In the aromatic compounds (A1-1), the aromatic ring may be any of aromatic hydrocarbon rings and aromatic heterocyclic rings. Such aromatic hydrocarbon rings include, for example, benzene ring, and condensed carbon rings such as naphthalene, azulene, indacene, anthracene, phenanthrene, triphenylene, pyrene, and other condensed carbon rings each having two to ten condensed 4- to 7-membered carbon rings. The heterocyclic rings include, but are not limited to, heterocyclic rings each containing an oxygen atom as a heteroatom, such as furan, oxazole, isoxazole, and other 5-membered rings, 4-oxo-4H-pyran, and other 6-membered rings, benzofuran, isobenzofuran, 4-oxo-4H-chromene, and other condensed rings; heterocyclic rings each containing a sulfur atom as a heteroatom, such as thiophene, thiazole, isothiazole, thiadiazole, and other 5-membered rings, 4-oxo-4H-thiopyran, and other 6-membered rings, benzothiophene and other condensed rings; heterocyclic rings each containing a nitrogen atom as a heteroatom, such as pyrrole, pyrazole, imidazole, triazole, and other 5-membered rings, pyridine, pyridazine, pyrimidine, pyrazine, and other 6-membered rings, indole, quinoline, acridine, naphthyridine, quinazoline, purine, and other condensed rings.

The methylene group at the adjacent position to the aromatic ring may be a methylene group constituting a non-aromatic ring condensed to the aromatic ring. The compounds (A1-1) may each have both a methyl group and a methylene group at the adjacent position to an aromatic ring.

The aromatic compounds each having a methyl group at the adjacent position to an aromatic ring include, for example, aromatic hydrocarbons each having about one to six methyl groups substituted on an aromatic ring, such as toluene, xylene, 1-ethyl-4-methylbenzene, 1-ethyl-3-methylbenzene, 1-t-butyl-4-methylbenzene, 1-methoxy-4-methylbenzene, mesitylene, durene, methylnaphthalene, methylanthracene, and 4,4'-dimethylbiphenyl; and heterocyclic compounds each having about one to six methyl groups substituted on a heterocyclic ring, such as 2-methylfuran, 3-methylfuran, 3-methylthiophene, 2-methylpyridine, 3-methylpyridine, 4-methylpyridine, 2,4-dimethylpyridine, 2,4,6-trimethylpyridine, 4-methylindole, and 2-methylquinoline.

The aromatic compounds each having a methylene group at the adjacent position to an aromatic ring include, but are not limited to, aromatic hydrocarbons each having an alkyl group or substituted alkyl group containing two or more carbon atoms, such as ethylbenzene, propylbenzene, 1,4-diethylbenzene, and diphenylmethane; aromatic heterocyclic compounds each having an alkyl group or substituted alkyl group containing 2 or more carbon atoms, such as 2-ethylfuran, 3-propylthiophene, 4-ethylpyridine, and 4-butylquinoline; and compounds each having a non-aromatic ring condensed to an aromatic ring and having a methylene group in the non-aromatic ring at the adjacent position to the aromatic ring, such as dihydronaphthalene, indene, indan, tetralin, fluorene, acenaphthene, phenalene, indanone, and xanthene.

The non-aromatic compounds (A1–2) each having a methyl group or methylene group at the adjacent position to an unsaturated bond include, but are not limited to, (A1–2a) chain unsaturated hydrocarbons each having a methyl group or methylene group at the "allyl position", and (A1–2b) compounds each having a methyl group or methylene group at the adjacent position to a carbonyl group, its equivalent, a cyano group or a nitro group.

Examples of the chain unsaturated hydrocarbons (A1–2a) are propylene, 1-butene, 2-butene, 1-pentene, 1-hexene, 2-hexene, 1,5-hexadiene, 1-octene, 3-octene, undecatriene, and other chain unsaturated hydrocarbons each containing from about 3 to about 20 carbon atoms. Examples of the compounds (A1–2b) include ketones such as acetone, methyl ethyl ketone, acetophenone, acetylacetone, acetoacetic esters, α-acetyl-γ-butyrolactone, and other chain ketones (inclusive of ketoesters and ketolactones); cyclopentanone, cyclohexanone, cyclododecanone, and other cyclic ketones; aldehydes such as acetaldehyde, propionaldehyde, and phenylaldehyde; carboxylic acids and esters thereof, such as acetic acid, propionic acid, phenylacetic acid, malonic acid, succinic acid, glutaric acid, adipic acid, and esters of these acids; lactones such as β-propiolactone, γ-butyrolactone, δ-valerolactone, and ε-caprolactone; acid anhydrides such as adipic anhydride; amides such as N,N-dimethylacetamide; lactams such as β-propiolactam, γ-butyrolactam, δ-valerolactam, and ε-caprolactam; nitriles such as acetonitrile, propionitrile, malononitrile, and ethyl cyanoacetate; imines such as N-isopropylidenebenzylamine, and N-(1-methylbutylidene)butylamine; and nitro compounds such as nitromethane, and nitroethane.

The non-aromatic cyclic compounds (A2) each constitutively having a methylene group in their ring include, for example, (A2-1) cycloalkanes, (A2-2) cycloalkenes, and (A2–3) non-aromatic heterocyclic compounds.

The cycloalkenes (A2-1) include, but are not limited to, compounds each having a 3- to 30-membered cycloalkane ring, such as cyclopropane, cyclobutane, cyclopentane, cyclohexane, cycloheptane, cyclooctane, cyclononane, cyclodecane, cyclododecane, cyclotetradecane, cyclohexadecane, cyclotetracosane, cyclotriacontane, and derivatives of these compounds. Preferred cycloalkane rings include 5- to 30-membered cycloalkane rings, of which 5- to 20-membered cycloalkane rings are typically preferred.

The cycloalkenes (A2-2) include, but are not limited to, compounds each having a 3- to 30-membered cycloalkene ring, such as cyclopropene, cyclobutene, cyclopentene, cyclooctene, cyclohexene, 1-methyl-cyclohexene, isophorone, cycloheptene, cyclododecene, as well as cyclopentadiene, 1,3-cyclohexadiene, 1,5-cyclooctadiene, and other cycloalkadienes, cyclooctatriene and other cycloalkatrienes, and derivatives of these compounds. Preferred cycloalkenes include compounds each having a 3- to 20-membered ring, of which compounds each having a 3- to 12-membered ring are typically preferred.

The non-aromatic heterocyclic compounds (A2–3) include, but are not limited to, 5- or 6-membered cyclic compounds each having at least one hetero atom selected from nitrogen atoms, oxygen atoms, and sulfur atoms; and condensed heterocyclic compounds each having a 5- or 6-membered ring having the hetero atom and being condensed to an aromatic ring. Examples of such compounds are dihydrofuran, tetrahydrofuran, pyran, dihydropyran, tetrahydropyran, piperidine, piperazine, pyrrolidine, xanthene, and derivatives of these compounds.

Another ring (an aromatic or non-aromatic carbon ring or heterocyclic ring) may be condensed to the ring of the non-aromatic cyclic compounds (A2) while commonly possessing one or more atoms. In this case, a bridged ring may be formed. The compounds (A3) each having a methine carbon atom include, for example, (A3-1) cyclic compounds each having a methine group (i.e., a methine carbon-hydrogen bond) as a constitutional unit of a ring, and (A3-2) chain compounds each having a methine carbon atom.

The cyclic compounds (A3-1) include, for example, (A3-1a) bridged compounds each having at least one methine group, and (A3-1b) non-aromatic cyclic compounds (e.g., alicyclic hydrocarbons) each having a hydrocarbon group combined with their ring. The bridged compounds also include compounds, in which two rings commonly possess two carbon atoms, such as hydrogenated products of condensed polycyclic aromatic hydrocarbons.

The bridged compounds (A3-1a) include, but are not limited to, decalin, bicyclo[2.2.0]hexane, bicyclo[2.2.2] octane, bicyclo[3.2.1]octane, bicyclo[4.3.2]undecane, bicyclo[3.3.3]undecane, thujone, carane, pinane, pinene, bornane, bornylene, norbornane, norbornene, camphor, camphoric acid, camphene, tricyclene, tricyclo[$5.2.1.0^{3,8}$] decane, tricyclo[$4.2.1.1^{2,5}$]decane, exotricyclo[$5.2.1.0^{2,6}$] decane, endotricyclo[$5.2.1.0^{2,6}$]decane, tricyclo[$4.3.1.1^{2,5}$] undecane, tricyclo[$4.2.2.1^{2,5}$] undecane, endotricyclo [$5.2.2.0^{2,6}$]undecane, adamantane, 1-adamantanol, 1-chloroadamantane, 1-methyladamantane, 1,3-dimethyladamantane, 1-methoxyadamantane, 1-carboxyadamantane, 1-methoxycarbonyladamantane, 1-nitroadamantane, tetracyclo[$4.4.0.1^{2,5}.1^{7,10}$] dodecane, perhydroanthracene, perhydroacenaphthene, perhydrophenanthrene, perhydrophenalene, perhydroindene, quinuclidine, and other bridged hydrocarbons or bridged heterocyclic compounds each having two to four rings, and derivatives thereof. These bridged compounds each have a methine carbon atom at a bridgehead position (corresponding to a junction position when two rings commonly possess two atoms).

The non-aromatic cyclic compounds (A3-1b) each having a hydrocarbon group combined with their ring include, but are not limited to, 1-methylcyclopentane, 1-methylcyclohexane, limonene, menthenes, menthol, carbomenthone, menthone, and other alicyclic hydrocarbons each having from about 3 to about 15 members and having a hydrocarbon group (e.g., an alkyl group) combined with its ring, and their derivatives. The hydrocarbon group just mentioned above may contain from about 1 to about 20 carbon atoms, and preferably from about 1 to about 10 carbon atoms. The non-aromatic cyclic compounds (A3-1b) each having a hydrocarbon group combined with a ring have a methine carbon atom at the bonding position between the ring and the hydrocarbon group.

The chain compounds (open-chain compounds) (A3-2) each having a methine carbon atom include, but are not limited to, chain hydrocarbons each having a tertiary carbon atom, such as isobutane, isopentane, isohexane, 3-methylpentane, 2,3-dimethylbutane, 2-methylhexane, 3-methylhexane, 3,4-dimethylhexane, 3-methyloctane, and other aliphatic hydrocarbons each containing from about 4 to about 20 carbon atoms, and preferably from about 4 to about 10 carbon atoms, and derivatives thereof.

The compounds (A) capable of generating a free radical further include methane, ethane, propane, butane, pentane, hexane, heptane, octane, decane, dodecane, tetradecane, octadecane, other straight-chain alkanes each containing from about 1 to about 20 carbon atoms, and other straight-chain alkanes.

Esters and Salts of Nitrous Acid (B)

At least one of esters of nitrous acid (nitrous esters) and salts of nitrous acid (nitrites) (hereinafter may briefly referred to as "nitrous ester and/or nitrite (B)") is used as a reacting agent in the present invention. Each of these nitrous esters and nitrites can be used alone or in combination.

Such nitrous esters include, but are not limited to, methyl nitrite, ethyl nitrite, propyl nitrite, isopropyl nitrite, butyl nitrite, isobutyl nitrite, t-butyl nitrite, amyl nitrite, isoamyl nitrite, t-amyl nitrite, hexyl nitrite, and other alkyl nitrites; phenyl nitrite, and other aryl nitrites; benzyl nitrite, and other aralkyl nitrites. Preferred nitrous esters include $C_1$–$C_6$ alkyl nitrites, and other alkyl nitrites. The nitrites (nitrous acid salts) include, but are not limited to, ammonium nitrite; lithium nitrite, sodium nitrite, potassium nitrite, and other alkali metal salts of nitrous acid; magnesium nitrite, calcium nitrite, barium nitrite, and other alkaline earth metal salts of nitrous acid; zinc nitrite, and other metal salts of nitrous acid.

The nitrous ester and/or nitrite may be supplied to the reaction system as intact or in the form of a solution prepared by dissolving the nitrous ester and/or nitrite in an appropriate solvent. The nitrous ester and/or nitrite can be formed within the reaction system. For example, a corresponding nitrous ester can be formed by adding an alcohol and a nitrogen oxide such as NO and $N_2O_3$ to system, or by adding an alcohol, a metal salt of nitrous acid, and an acid to the reaction system.

Reactions

The reaction is performed in the presence of, or in the absence of, a solvent. The solvent can be any solvent that is inert under reaction conditions. Such solvents include, but are not limited to, acetic acid, propionic acid, trifluoroacetic acid, and other organic acids; acetonitrile, propionitrile, benzonitrile, and other nitrites; formamide, acetamide, dimethylformamide (DMF), dimethylacetamide, and other amides; hexane, octane, and other aliphatic hydrocarbons; chloroform, dichloromethane, dichloroethane, carbon tetrachloride, chlorobenzene, trifluoromethylbenzene, and other halogenated hydrocarbons; nitrobenzene, nitromethane, nitroethane, and other nitro compounds; ethyl acetate, butyl acetate, and other esters; and mixtures of these solvents. Among them, acetic acid and other organic acids, acetonitrile, benzonitrile, and other nitrites, trifluoromethylbenzene, and other halogenated hydrocarbons, ethyl acetate and other esters are often used as the solvent.

The ratio of the radical-formable compound (A) to the nitrous ester and/or nitrite (B) can appropriately be selected depending on the types (costs and reactivity) and combinations of the two compounds. For example, the radical-formable compound (A) may be used in an equivalent amount or in excess (e.g., from about 1.1 to about 50 times by equivalent or more, preferably from about 3 to 30 times by equivalent) to the nitrous ester and/or nitrite (B). Alternatively, the nitrous ester and/or nitrite (B) may be used in excess to the radical-formable compound (A).

The process of the present invention has a feature in that the reaction smoothly proceeds even under mild conditions. A reaction temperature can be appropriately selected depending on the types of the compound (A), the nitrous ester and/or nitrite (B), and the nitrogen-containing cyclic compound or the type of the target product, and is, for example, from about 0° C. to about 250° C., preferably from about 25° C. to 150° C., and more preferably from about 40° C. to about 120° C. The reaction may be performed in an atmosphere of an inert gas such as nitrogen gas or argon gas or in an atmosphere of the air or oxygen gas depending on the type of the target product and other conditions. The reaction can be performed at atmospheric pressure or under a pressure (under a load) according to a conventional procedure such as batch system, semi-batch system, or continuous system such as multistage continuous circulation system.

The process of the present invention produces, for example, oxime compounds each having a hydroxyimino group combined with a radical-generating site of the radical-formable compound (A) (substrate), nitro compounds each having a nitro group combined with the radical-generating site; nitrile compounds each having a nitrilo group combined with the radical-generating site, nitroso compounds having a nitroso group combined with the radical-generating site, and dimers thereof (di-N-oxide compounds having two molecules of a nitroso compound combined through their nitrogen atom), and other nitrogen-containing organic compounds (organic compounds each having a nitrogen-atom-containing group); hydroxyl compounds each having a hydroxyl group combined with the radical-generating site; carbonyl compounds each having an oxo group combined with the radical-generating site; ester compounds each having an acyloxy group combined with the radical-generating site (for example, when an organic acid such as acetic acid is used as the solvent), and other oxygen-containing organic compounds (organic compounds each having an oxygen-atom-containing group); and unsaturated compounds each having a double bond formed between the radical-generating site and the adjacent position thereto (organic compounds each having a carbon-carbon unsaturated bond-containing group).

For example, when cyclohexane is used as the substrate, cyclohexanone oxime, nitrosocyclohexanone, its dimer (nitrosocyclohexanone dimer), nitrocyclohexane, cyclohexanone, and/or cyclohexyl acetate (when acetic acid is used as the solvent) can be formed. When toluene is used as the substrate, benzaldehyde oxime, nitromethylbenzene, benzaldehyde, benzyl acetate, benzonitrile, nitrosotoluene, and/or nitrosotoluene dimer can be formed. When isopropylbenzene is used as the substrate, isopropenylbenzene, α,α-dimethylbenzyl alcohol, and/or (1-methyl-1-nitroethyl) benzene can be formed.

The proportions of the resulting products can be controlled by appropriately selecting reaction conditions such as the reaction temperature, reaction time, the type and amount of the catalyst, the type of the solvent, the ratio of the radical-formable compound (A) to the nitrous ester and/or nitrite (B). In general, the compounds (A1) and (A2), and other substrates having a methyl group or methylene group as the radical-generating site yield oxime compounds, nitroso compounds and dimers thereof as major products. The compounds (A3), and other substrates having a methine group as the radical-generating site yield unsaturated compounds as major products. The mechanism is probably as follows. For example, when cyclohexane is allowed to react with a nitrous ester and/or nitrite, nitrosocyclohexane is initially formed, and nitrosocyclohexane undergoes rearrangement to thereby yield cyclohexanone oxime. Some of the nitroso compounds are in reversible equilibrium with corresponding dimers (di-N-oxide compounds derived from two molecules of the nitroso compound combined through their nitrogen atom), and the equilibrium lies to the dimers. When the reaction is performed for a long time, such a nitroso compound and its dimer are formed in a trace amount in a yield of up to less than 1%. These oxime compounds and unsaturated compounds may be probably formed via nitroso compounds as intermediates.

As a preferred embodiment of the process of the present invention, the nitrous ester and/or nitrite (B) is added intermittently in plural installments or continuously to the reaction system. By this procedure, second reactions are suppressed specifically in nitroso-conversion, and thereby a nitroso compound or its dimer can be formed with a higher selectivity than the case when the nitrous ester and/or nitrite (B) is added as a single unit (by one operation). Accordingly, an oxime compound and other target products can be obtained in a high yield as a result of, for example, a subsequent rearrangement reaction.

An oxime compound can be prepared by a single step but it is preferably prepared by two steps including allowing the radical-formable compound (A) to react with the nitrous ester and/or nitrite (B) to thereby form a nitroso compound or its dimer; and converting the formed nitroso compound or its dimer into an oxime compound. This process can significantly shorten a total reaction time by adding an additive to the reaction system or by heating the reaction system in the latter converting step (a rearrangement process of the nitroso compound). More specifically, the reaction time can be shortened to one fifth to one thirtieth. By adding an additive to the reaction system or heating the reaction system, the yield of the nitroso compound and its dimer can be reduced to a trace amount or in a yield of up to less than 1%.

Such additives used herein are not specifically limited as long as they can induce rearrangement of a nitroso form to an oxime form. Acids and bases are preferably used as the additives. Such acids include, but are not limited to, methanesulfonic acid, trifluoromethanesulfonic acid, benzenesulfonic acid, p-toluenesulfonic acid, and other sulfonic acids; sulfuric acid, nitric acid, hydrogen chloride, phosphoric acids, boric acids, fuming sulfuric acid, and other mineral acids; aluminum chloride, zinc chloride, scandium triflate, and other Lewis acids; silica, alumina, zeolite, and other solid acids; phosphomolybdic acid, phosphotungstic acid, silicomolybdic acid, silicotungstic acid, other polyacids, and other complex acids; and strongly acidic cationic ion exchange resins. Examples of the bases are triethylamine, and other tertiary amines, pyridine, and other nitrogen-containing heterocyclic compounds, sodium acetate, sodium methoxide, and other organic bases; sodium carbonate, sodium hydrogencarbonate, sodium hydroxide, potassium hydroxide, and other inorganic bases; magnesium oxide, hydrotalcite, hydroxyapatite, and other solid bases. These additives can be added in a single unit or in plural installments. The amount of the additive(s) is, for example, from about 0.01 to about 100 parts by weight, preferably from about 0.1 to about 50 parts by weight, and more preferably from about 0.3 to about 30 parts by weight relative to 100 parts by weight of the radical-formable compound (A).

Such a rearrangement reaction using the additive is performed at a temperature of, for example, from about 40° C. to about 120° C., and preferably from about 50° C. to about 100° C. for about 5 to about 60 minutes, and preferably about 10 to about 50 minutes. The rearrangement reaction by heating is performed at a temperature of, for example, from about 120° C. to about 250° C., and preferably from about 150° C. to about 200° C. for about 0.5 to about 30 minutes, and preferably about 2 to about 15 minutes.

After the completion of the reaction, reaction products can be separated and purified by a separation means such as filtration, concentration, distillation, extraction, crystallization, recrystallization, adsorption, column chromatography, and combinations of these separation means.

EXAMPLES

The present invention will be illustrated in further detail with reference to several examples and comparative examples below, which are not intended to limit the scope of the invention. All yields are on the basis of a nitrous ester or nitrite. Reaction mixtures were analyzed by gas chromatography or high-performance liquid chromatography.

Example 1

Cyclopentane (1 ml), t-butyl nitrite (1 mmol), N-hydroxyphthalimide (0.2 mmol), and acetic acid (1 ml) were placed in a flask and were stirred at 80° C. in an atmosphere of argon gas (1 atm=0.101 MPa) for 20 hours. The resulting reaction mixture was analyzed to find that cyclopentanone oxime, nitrocyclopentane, cyclopentanone, and cyclopentyl acetate were formed in yields of 4%, 2%, 3%, and less than 1%, respectively.

Example 2

Cyclohexane (1 ml), t-butyl nitrite (1 mmol), N-hydroxyphthalimide (0.2 mmol), and acetic acid (1 ml) were placed in a flask and were stirred at 80° C. in an atmosphere of argon gas (1 atm=0.101 MPa) for 20 hours. The resulting reaction mixture was analyzed to find that cyclohexanone oxime, nitrocyclohexane, cyclohexanone, and cyclohexyl acetate were formed in yields of 16%, 10%, 3%, and 2%, respectively.

Example 3

Cyclohexane (1 ml), t-butyl nitrite (1 mmol), 4-chloro-N-hydroxyphthalimide (0.2 mmol), and acetic acid (1 ml) were placed in a flask and were stirred at 80° C. in an atmosphere of argon gas (1 atm=0.101 MPa) for 20 hours. The resulting reaction mixture was analyzed to find that cyclohexanone oxime, nitrocyclohexane, cyclohexanone, and cyclohexyl acetate were formed in yields of 13%, 9%, 2%, and 2%, respectively.

Example 4

Cyclohexane (1 ml), t-butyl nitrite (1 mmol), 4-chloro-N-hydroxyphthalimide (0.2 mmol), and acetic acid (1 ml) were placed in a flask and were stirred at 100° C. in an atmosphere of argon gas (1 atm=0.101 MPa) for 20 hours. The resulting reaction mixture was analyzed to find that cyclohexanone oxime, nitrocyclohexane, cyclohexanone, and cyclohexyl acetate were formed in yields of 26%, 4%, 4%, and in a trace amount, respectively.

Example 5

Cycloheptane (1 ml), t-butyl nitrite (1 mmol), N-hydroxyphthalimide (0.2 mmol), and acetic acid (1 ml) were placed in a flask and were stirred at 80° C. in an atmosphere of argon gas (1 atm=0.101 MPa) for 20 hours. The resulting reaction mixture was analyzed to find that cycloheptanone oxime, nitrocycloheptane, cycloheptanone, and cycloheptyl acetate were formed in yields of 21%, 3%, 7%, and less than 1%, respectively.

Example 6

Cycloheptane (1 ml), t-butyl nitrite (1 mmol), 4-chloro-N-hydroxyphthalimide (0.2 mmol), and acetic acid (1 ml) were placed in a flask and were stirred at 80° C. in an atmosphere of argon gas (1 atm=0.101 MPa) for 20 hours. The resulting reaction mixture was analyzed to find that cycloheptanone oxime, nitrocycloheptane, cycloheptanone, and cycloheptyl acetate were formed in yields of 16%, 4%, 6%, and less than 1%, respectively.

Example 7

Cyclooctane (1 ml), t-butyl nitrite (1 mmol), N-hydroxyphthalimide (0.2 mmol), and acetic acid (1 ml) were placed in a flask and were stirred at 80° C. in an atmosphere of argon gas (1 atm=0.101 MPa) for 20 hours. The resulting reaction mixture was analyzed to find that cyclooctanone oxime, nitrocyclooctane, and cyclooctanone were formed in yields of 55%, 5%, and 4%, respectively.

Example 8

Cyclooctane (2 ml), t-butyl nitrite (1 mmol), N-hydroxyphthalimide (0.2 mmol), and acetic acid (1 ml) were placed in a flask and were stirred at 80° C. in an atmosphere of argon gas (1 atm=0.101 MPa) for 20 hours. The resulting reaction mixture was analyzed to find that cyclooctanone oxime, nitrocyclooctane, and cyclooctanone were formed in yields of 64%, 4%, and 2%, respectively.

Example 9

Cyclododecane (1 ml), t-butyl nitrite (1 mmol), N-hydroxyphthalimide (0.2 mmol), and acetic acid (1 ml) were placed in a flask and were stirred at 80° C. in an atmosphere of argon gas (1 atm=0.101 MPa) for 20 hours. The resulting reaction mixture was analyzed to find that cyclododecanone oxime, nitrocyclododecane, and cyclododecanone were formed in yields of 41%, 4%, and 9%, respectively.

Example 10

Toluene (1 ml), t-butyl nitrite (1 mmol), N-hydroxyphthalimide (0.2 mmol), and acetic acid (1 ml)

were placed in a flask and were stirred at 60° C. in an atmosphere of argon gas (1 atm=0.101 MPa) for 20 hours. The resulting reaction mixture was analyzed to find that benzaldehyde oxime, nitromethylbenzene, benzaldehyde, benzyl acetate, and benzonitrile were formed in yields of 28%, 4%, 4%, 3%, and 3%, respectively.

Example 11

Toluene (1 ml), t-butyl nitrite (1 mmol), 4-chloro-N-hydroxyphthalimide (0.2 mmol), and acetic acid (1 ml) were placed in a flask and were stirred at 100° C. in an atmosphere of argon gas (1 atm=0.101 MPa) for 20 hours. The resulting reaction mixture was analyzed to find that benzaldehyde oxime, nitromethylbenzene, benzaldehyde, benzyl acetate, and benzonitrile were formed in yields of 5%, 2%, 9%, 5%, and 10%, respectively.

Example 12

In a flask p-xylene (1 ml), t-butyl nitrite (1 mmol), N-hydroxyphthalimide (0.1 mmol), and acetic acid (1 ml) were placed and were stirred at 80° C. in an atmosphere of argon gas (1 atm=0.101 MPa) for 20 hours. The resulting reaction mixture was analyzed to find that p-methylbenzaldehyde oxime, p-methylbenzaldehyde, and p-methylbenzonitrile were formed in yields of 55%, 4%, and 5%, respectively.

Comparative Example 1

The procedure of Example 12 was repeated, except that N-hydroxyphthalimide was not used. As a result, no reaction proceeded.

Example 13

In a flask p-xylene (1 ml), t-butyl nitrite (1 mmol), N-hydroxyphthalimide (0.2 mmol), and acetic acid (1 ml) were placed and were stirred at 60° C. in an atmosphere of argon gas (1 atm=0.101 MPa) for 20 hours. The resulting reaction mixture was analyzed to find that p-methylbenzaldehyde oxime, p-methylbenzaldehyde, and p-methylbenzonitrile were formed in yields of 68%, 3%, and 5%, respectively.

Example 14

In a flask p-xylene (1 ml), t-butyl nitrite (1 mmol), N-hydroxyphthalimide (0.1 mmol), and acetic acid (1 ml) were placed and were stirred at 60° C. in an atmosphere of argon gas (1 atm=0.101 MPa) for 20 hours. The resulting reaction mixture was analyzed to find that p-methylbenzaldehyde oxime, p-methylbenzaldehyde, and p-methylbenzonitrile were formed in yields of 60%, 3%, and 3%, respectively.

Example 15

Ethylbenzene (1 ml), t-butyl nitrite (1 mmol), N-hydroxyphthalimide (0.2 mmol), and acetic acid (1 ml) were placed in a flask and were stirred at 100° C. in an atmosphere of argon gas (1 atm=0.101 MPa) for 20 hours. The resulting reaction mixture was analyzed to find that acetophenone oxime, (1-nitroethyl)benzene, acetophenone, and α-methylbenzyl acetate were formed in yields of 32%, 5%, 23%, and 15%, respectively.

Example 16

Ethylbenzene (1 ml), t-butyl nitrite (1 mmol), N-hydroxyphthalimide (0.2 mmol), and acetic acid (1 ml) were placed in a flask and were stirred at 80° C. in an atmosphere of argon gas (1 atm=0.101 MPa) for 20 hours. The resulting reaction mixture was analyzed to find that acetophenone oxime, (1-nitroethyl)benzene, acetophenone, and α-methylbenzyl acetate were formed in yields of 47%, 4%, 17%, and 14%, respectively.

Example 17

Mesitylene (1 ml), t-butyl nitrite (1 mmol), N-hydroxyphthalimide (0.2 mmol), and acetic acid (1 ml) were placed in a flask and were stirred at 60° C. in an atmosphere of argon gas (1 atm=0.101 MPa) for 20 hours. The resulting reaction mixture was analyzed to find that 3,5-dimethylbenzaldehyde oxime, 3,5-dimethylbenzaldehyde, 3,5-dimethylbenzonitrile, and 3,5-dimethylphenylmethyl acetate were formed in yields of 61%, 3%, 4%, and less than 1%, respectively.

Example 18

Isopropylbenzene (1 ml), t-butyl nitrite (1 mmol), N-hydroxyphthalimide (0.2 mmol), and acetic acid (1 ml) were placed in a flask and were stirred at 80° C. in an atmosphere of argon gas (1 atm=0.101 MPa) for 20 hours. The resulting reaction mixture was analyzed to find that isopropenylbenzene, (1-hydroxy-1-methylethyl)benzene, and (1-methyl-1-nitroethyl)benzene were formed in yields of 60%, 6%, and 7%, respectively.

Comparative Example 2

The procedure of Example 18 was repeated, except that N-hydroxyphthalimide was not used. As a result, isopropenylbenzene, (1-hydroxy-1-methylethyl)benzene, and (1-methyl-1-nitroethyl)benzene were formed in yields of less than 1%, 2%, and 6%, respectively.

Example 19

Cyclooctane (1 ml; 7.4 mmol), N-hydroxyphthalimide (0.2 mmol), sodium nitrite (1 mmol), and acetic acid (1 ml) were placed in a flask and were stirred at 100° C. in an atmosphere of argon gas (1 atm=0.101 MPa) for 20 hours. The resulting reaction mixture was analyzed to find that cyclooctanone oxime was formed in a yield of 10%.

Example 20

Cyclododecane (1.66 g; 9.88 mmol), t-butylnitrite (2 mmol), N-hydroxyphthalimide (0.4 mmol), and acetic acid (2 ml) were placed in a flask and were stirred at 80° C. in an atmosphere of argon gas for 1 hour. The resulting mixture was further treated with sulfuric acid having a concentration of 98% by weight (200 mg) with stirring at 70° C. for 15 minutes. The reaction mixture was neutralized with sodium hydroxide and was analyzed to find that cyclododecanone oxime, nitrocyclododecane, and cyclododecanone were formed in yields of 41%, 6%, and 7%, respectively.

Example 21

Cyclododecane (1.66 g; 9.88 mmol), t-butylnitrite (2 mmol), N-hydroxyphthalimide (0.4 mmol), and acetic acid (2 ml) were placed in a flask and were stirred at 80° C. in an atmosphere of argon gas for 1 hour. The mixture was further treated with fuming sulfuric acid having a concentration of 5% by weight (100 mg) with stirring at 70° C. for 15 minutes under anhydrous conditions. The reaction mixture was neutralized with sodium hydroxide and was analyzed to find that cyclododecanone oxime, nitrocyclododecane, and cyclododecanone were formed in yields of 48%, 6%, and 3%, respectively.

Example 22

Cyclododecane (1.66 g; 9.88 mmol), t-butylnitrite (2 mmol), N-hydroxyphthalimide (0.4 mmol), and acetic acid (2 ml) were placed in a flask and were stirred at 80° C. in an atmosphere of argon gas for 1 hour. The resulting reaction mixture was analyzed to find that cyclododecanone oxime, nitrosocyclododecane dimer, nitrocyclododecane, and cyclododecanone were formed in yields of 10%, 38%, 6%, and 3%, respectively.

Example 23

Cyclododecane (1.66 g; 9.88 mmol), t-butylnitrite (2 mmol), N-hydroxyphthalimide (0.4 mmol), and acetic acid (2 ml) were placed in a flask and were stirred at 80° C. in an atmosphere of argon gas for 1 hour. The resulting mixture was further treated with sulfuric acid having a concentration of 98% by weight (50 mg) with stirring at 70° C. for 15 minutes. The reaction mixture was neutralized with sodium hydroxide and was analyzed to find that cyclododecanone oxime, nitrocyclododecane, and cyclododecanone were formed in yields of 39%, 7%, and 5%, respectively.

Example 24

Cyclododecane (1.66 g; 9.88 mmol), t-butylnitrite (2 mmol), N-hydroxyphthalimide (0.4 mmol), and acetic acid (2 ml) were placed in a flask and were stirred at 80° C. in an atmosphere of argon gas for 1 hour. The resulting mixture was further treated with triethylamine (300 mg) with stirring at 80° C. for 30 minutes. The resulting reaction mixture was analyzed to find that cyclododecanone oxime, nitrocyclododecane, and cyclododecanone were formed in yields of 39%, 7%, and 5%, respectively.

Example 25

Cyclohexane (2 ml), t-butyl nitrite (2 mmol), N-hydroxyphthalimide (0.4 mmol), and acetic acid (2 ml) were placed in a flask and were stirred at 100° C. in an atmosphere of argon gas for 2 hours. The resulting mixture was further treated with sulfuric acid having a concentration of 98% by weight (200 mg) with stirring at 70° C. for 15 minutes. The reaction mixture was then neutralized with sodium hydroxide and was analyzed to find that cyclohexanone oxime, nitrocyclohexane, and cyclohexanone were formed in yields of 28%, 4%, and 5%, respectively.

Example 26

Cyclohexane (2 ml), t-butyl nitrite (2 mmol), N-hydroxyphthalimide (0.4 mmol), and acetic acid (2 ml) were placed in a flask and were stirred at 100° C. in an atmosphere of argon gas for 2 hours. The resulting mixture was further treated with triethylamine (300 mg) with stirring at 80° C. for 30 minutes. The reaction mixture was analyzed to find that cyclohexanone oxime, nitrocyclohexane, and cyclohexanone were formed in yields of 25%, 3%, and 4%, respectively.

Example 27

Cyclododecane (1.66 g; 9.88 mmol), t-butylnitrite (2 mmol), N-hydroxyphthalimide (0.4 mmol), and acetic acid (2 ml) were placed in a flask and were stirred at 80° C. in an atmosphere of argon gas for 1 hour. The resulting mixture was further treated with zinc chloride (20 mg) with stirring at 80° C. for 30 minutes. The reaction mixture was neutralized with sodium hydroxide and was then analyzed to find that cyclododecanone oxime, nitrocyclododecane, and cyclododecanone were formed in yields of 35%, 7%, and 3%, respectively.

Example 28

Cyclododecane (1.66 g; 9.88 mmol), t-butylnitrite (2 mmol), N-hydroxyphthalimide (0.4 mmol), and acetic acid (2 ml) were placed in a flask and were stirred at 80° C. in an atmosphere of argon gas for 1 hour. The resulting mixture was further treated with scandium triflate (20 mg) with stirring at 80° C. for 30 minutes. The reaction mixture was neutralized with sodium hydroxide and was then analyzed to find that cyclododecanone oxime, nitrocyclododecane, and cyclododecanone were formed in yields of 40%, 7%, and 3%, respectively.

Example 29

Cyclododecane (1.66 g; 9.88 mmol), t-butylnitrite (2 mmol), N-hydroxyphthalimide (0.4 mmol), and acetic acid (2 ml) were placed in a flask and were stirred at 80° C. in an atmosphere of argon gas for 1 hour. The resulting mixture was further stirred at 180° C. for 5 minutes and was then analyzed to find that cyclododecanone oxime, nitrocyclododecane, and cyclododecanone were formed in yields of 28%, 10%, and 3%, respectively.

Example 30

Cyclododecane (3.32 g; 19.8 mmol), N-hydroxyphthalimide (0.8 mmol), and acetic acid (4 ml) were placed in a flask, t-butyl nitrite (4 mmol) was added to the mixture in four installments of 1 mmol each once every 30 minutes with stirring at 70° C. in an atmosphere of argon gas for a total of 2.5 hours. The mixture was further treated with sulfuric acid having a concentration of 98% by weight (200 mg) with stirring at 70° C. for 15 minutes, was neutralized with sodium hydroxide and was analyzed to find that cyclododecanone oxime, nitrocyclododecane, and cyclododecanone were formed in yields of 65%, 2%, and 5%, respectively.

Example 31

Cyclododecane (3.32 g; 19.8 mmol), N-hydroxyphthalimide (0.8 mmol), and acetic acid (4 ml) were placed in a flask, t-butyl nitrite (4 mmol) was added dropwise to the mixture with stirring at 70° C. in an atmosphere of argon gas over 2.5 hours. After the completion of the reaction, the reaction mixture was further treated with sulfuric acid having a concentration of 98% by weight (200 mg) with stirring at 70° C. for 15 minutes, was neutralized with sodium hydroxide and was analyzed to find that cyclododecanone oxime, nitrocyclododecane, and cyclododecanone were formed in yields of 67%, 2%, and 4%, respectively.

Example 32

Cyclododecane (3.32 g; 19.8 mmol), N-hydroxyphthalimide (0.8 mmol), and acetic acid (4 ml) were placed in a flask, t-butyl nitrite (4 mmol) was added to the mixture in four installments of 1 mmol each once every 30 minutes with stirring at 70° C. in an atmosphere of argon gas for a total of 2.5 hours. The reaction mixture was analyzed to find that cyclododecanone oxime, nitrosocyclododecane dimer, nitrocyclododecane, and cyclododecanone were formed in yields of 11%, 60%, 1%, and 1%, respectively.

Example 33

Cyclohexane (2 ml), t-butyl nitrite (4 mmol), N-hydroxyphthalimide (0.4 mmol), and acetic acid (2 ml) were placed in a flask and were stirred at 100° C. in an atmosphere of argon gas for 2.5 hours. The resulting mixture was further treated with sulfuric acid having a concentration of 98% by weight (200 mg) with stirring at 70° C. for 15 minutes. The reaction mixture was then neutralized with sodium hydroxide and was analyzed to find that cyclohexanone oxime, nitrocyclohexane, and cyclohexanone were formed in yields of 38%, 2%, and 5%, respectively.

Example 34

Cyclohexane (2 ml), t-butyl nitrite (4 mmol), N-hydroxyphthalimide (0.4 mmol), and acetic acid (2 ml) were placed in a flask and were stirred at 70° C. in an atmosphere of argon gas for 2.5 hours. The resulting reaction mixture was analyzed to find that cyclohexanone oxime, nitrosocyclohexane dimer, nitrocyclohexane, and cyclohexanone were formed in yields of 2%, 25%, 2%, and 5%, respectively.

Example 35

Toluene (2 ml), t-butyl nitrite (4 mmol), N-hydroxyphthalimide (0.4 mmol), and acetic acid (2 ml) were placed in a flask and were stirred at 70° C. in an atmosphere of argon gas for 2.5 hours. The resulting mixture was further treated with sulfuric acid having a concentration of 98% by weight (200 mg) with stirring at 60° C. for 15 minutes. The reaction mixture was then neutralized with sodium hydroxide and was analyzed to find that benzaldehyde oxime, nitromethylbenzene, and benzaldehyde were formed in yields of 65%, 2%, and 3%, respectively.

Example 36

Ethylbenzene (2 ml), t-butyl nitrite (4 mmol), N-hydroxyphthalimide (0.4 mmol), and acetic acid (2 ml) were placed in a flask and were stirred at 80° C. in an atmosphere of argon gas for 2.5 hours. The resulting mixture was further treated with sulfuric acid having a concentration of 98% by weight (200 mg) with stirring at 70° C. for 15 minutes. The reaction mixture was then neutralized with sodium hydroxide and was analyzed to find that acetophenone oxime, (1-nitroethyl)benzene, acetophenone, and α-methylbenzyl acetate were formed in yields of 61%, 1%, 8%, and 5%, respectively.

Example 37

Cyclododecane (3.32 g; 19.8 mmol), N-hydroxyphthalimide (0.8 mmol), and acetic acid (4 ml) were placed in a flask, t-butyl nitrite (6 mmol) was added to the mixture in six installments of 1 mmol each once every 30 minutes with stirring at 70° C. in an atmosphere of argon gas for a total of 3.5 hours. The resulting mixture was further treated with sulfuric acid having a concentration of 98% by weight (200 mg) with stirring at 70° C. for 15 minutes. The reaction mixture was then neutralized with sodium hydroxide and was analyzed to find that cyclododecanone oxime, nitrocyclododecane, and cyclododecanone were formed in yields of 52%, 3%, and 6%, respectively.

Example 38

Cyclododecane (3.32 g; 19.8 mmol), N-hydroxyphthalimide (0.8 mmol), and acetic acid (4 ml) were placed in a flask, t-butyl nitrite (4 mmol) was added to the mixture in four installments of 1 mmol each once every 15 minutes with stirring at 70° C. in an atmosphere of argon gas for a total of 1.5 hours. The resulting mixture was further treated with sulfuric acid having a concentration of 98% by weight (200 mg) with stirring at 70° C. for 15 minutes. The reaction mixture was then neutralized with sodium hydroxide and was analyzed to find that cyclododecanone oxime, nitrocyclododecane, and cyclododecanone were formed in yields of 62%, 2%, and 5%, respectively.

Example 39

Cyclododecane (3.32 g; 19.8 mmol), N-hydroxyphthalimide (0.8 mmol), and acetic acid (4 ml) were placed in a flask, t-butyl nitrite (4 mmol) was added to the mixture in two installments of 2 mmol each once every 1 hour with stirring at 70° C. in an atmosphere of argon gas for a total of 2 hours. The resulting mixture was further treated with sulfuric acid having a concentration of 98% by weight (200 mg) with stirring at 70° C. for 15 minutes. The reaction mixture was then neutralized with sodium hydroxide and was analyzed to find that cyclododecanone oxime, nitrocyclododecane, and cyclododecanone were formed in yields of 60%, 2%, and 5%, respectively.

Example 40

Cyclododecane (3.32 g; 19.8 mmol), N-hydroxyphthalimide (0.8 mmol), and acetic acid (4 ml) were placed in a flask, n-butyl nitrite (4 mmol) was added to the mixture in four installments of 1 mmol each once every 30 minutes with stirring at 70° C. in an atmosphere of argon gas for a total of 2.5 hours. The resulting mixture was further treated with sulfuric acid having a concentration of 98% by weight (200 mg) with stirring at 70° C. for 15 minutes. The reaction mixture was then neutralized with sodium hydroxide and was analyzed to find that cyclododecanone oxime, nitrocyclododecane, and cyclododecanone were formed in yields of 41%, 6%, and 6%, respectively.

Example 41

Cyclododecane (3.32 g; 19.8 mmol), 4-lauryloxycarbonyl-N-hydroxyphthalimide (0.8 mmol), and acetic acid (1 ml) were placed in a flask, t-butyl nitrite (4 mmol) was added to the mixture in four installments of 1 mmol each once every 30 minutes with stirring at 70° C. in an atmosphere of argon gas for a total of 2.5 hours. The resulting mixture was further treated with sulfuric acid having a concentration of 98% by weight (200 mg) with stirring at 70° C. for 15 minutes. The reaction mixture was then neutralized with sodium hydroxide and was analyzed to find that cyclododecanone oxime, nitrocyclododecane, and cyclododecanone were formed in yields of 41%, 6%, and 4%, respectively.

Example 42

Cyclododecane (3.32 g; 19.8 mmol), t-butyl nitrite (1 mmol), and 4-lauryloxycarbonyl-N-hydroxyphthalimide (0.5 mmol) were placed in a flask and were stirred at 70° C. in an atmosphere of argon gas for 2 hours. The resulting mixture was diluted with ether (2 ml) and was further treated with sulfuric acid having a concentration of 98% by weight (200 mg) with stirring at 70° C. for 15 minutes. The reaction mixture was then neutralized with sodium hydroxide and was analyzed to find that cyclododecanone oxime, nitrocyclododecane, and cyclododecanone were formed in yields of 58%, 5%, and 3%, respectively.

While the present invention has been described with reference to what are presently considered to be the preferred embodiments, it is to be understood that the invention is not limited to the disclosed embodiments. On the contrary, the invention is intended to cover various modifications and equivalent arrangements included within the spirit and scope of the appended claims. The scope of the following claims is to be accorded the broadest interpretation so as to encompass all such modifications and equivalent structures and functions.

What is claimed is:

1. A process for producing an organic compound, the process comprising the step of allowing
   (A) a compound capable of generating a free radical, said compound being selected from the group consisting of: (A1) aromatic compounds and unsaturated compounds each having a methyl group or methylene group at the adjacent position to an aromatic ring or an unsaturated bond; (A2) non-aromatic cyclic compounds each constitutively having a methylene group in their ring; (A3) compounds each having a methine carbon atom; and (A4) straight-chain alkanes, to react with
   (B) at least one of the alkyl nitrites, aryl nitrites, aralkyl nitrites, ammonium nitrites, and metal salts of nitrous acid in the presence of
     a nitrogen-containing cyclic compound constitutively having a skeleton represented by following Formula (i) in its ring:

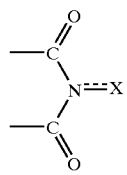

(i)

wherein X is one of an oxygen atom and an —OR group, and wherein R is one of a hydrogen atom and a hydroxyl-protecting group.

2. The process according to claim 1, wherein the nitrogen-containing cyclic compound is a cyclic imide compound having a cyclic imide skeleton represented by following Formula (I):

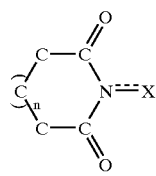

(I)

wherein n is one of 0 and 1; X is one of an oxygen atom and an —OR group, and wherein R is one of a hydrogen atom and a hydroxyl-protecting group.

3. The process according to claim 1, wherein the nitrogen-containing cyclic compound is a compound represented by following Formula (1):

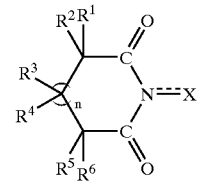

(1)

wherein n is one of 0 and 1;
X is one of an oxygen atom and an —OR group,
   wherein R is one of a hydrogen atom and a hydroxyl-protecting group; $R^1$, $R^2$, $R^3$, $R^4$, $R^5$, and $R^6$ are the same or different and are each one of hydrogen atoms, halogen atoms, alkyl groups, aryl groups, cycloalkyl groups, hydroxyl groups, alkoxy groups, carboxyl groups, substituted oxycarbonyl groups, acyl groups, and acyloxy groups,
wherein at least two of $R^1$, $R^2$, $R^3$, $R^4$, $R^5$, and $R^6$ may be combined to form a double bond, an aromatic ring, or a non-aromatic ring with a carbon atom or a carbon-carbon bond constituting the cyclic imide skeleton, and
wherein one or more of an N-substituted cyclic imide group represented by following Formula (a):

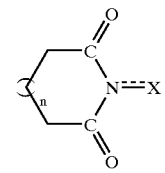

(a)

wherein n and X have the same meanings as defined above, may be further formed on at least one of $R^1$, $R^2$, $R^3$, $R^4$, $R^5$, and $R^6$ or at least one of the double bond, the aromatic ring and the non-aromatic ring formed by at least two of $R^1$, $R^2$, $R^3$, $R^4$, $R^5$, and $R^6$.

4. The process according to claim 1, wherein reactants (A) and (B) react to form an oxime compound.

5. The process according to claim 1, wherein the nitrite (B) is added to a reaction system intermittently in plural installments or continuously.

6. The process according to claim 1, further comprising allowing the compound (A) capable of generating a free radical to react with the at least one of the alkyl nitrites, aryl nitrites, aralkyl nitrites, ammonium nitrates, and metal salts of nitrous acid (B) to thereby yield a nitroso compound or a dimer thereof.

7. The process according to claim 1, further comprising the steps of:
   allowing the compound (A) capable of generating a free radical to react with the at least one of the alkyl nitrites, aryl nitrites, aralkyl nitrites, ammonium nitrates, and metal salts of nitrous acid (B) to thereby yield a nitroso compound or a dimer thereof; and
   converting the formed nitroso compound or a dimer thereof into a corresponding oxime compound.

* * * * *